United States Patent
Constant et al.

(10) Patent No.: US 10,124,090 B2
(45) Date of Patent: Nov. 13, 2018

(54) EMBOLIC DEVICES

(71) Applicant: MicroVention, Inc., Tustin, CA (US)

(72) Inventors: Michael Constant, Mission Viejo, CA (US); Edward Michael Keeley, Huntington Beach, CA (US); Joshua Garretson, San Diego, CA (US); Gregory M. Cruise, Rancho Santa Margarita, CA (US); Wendy Graczyk, San Clemente, CA (US)

(73) Assignee: Terumo Corporation (JP)

( * ) Notice: Subject to any disclaimer, the term of this patent is extended or adjusted under 35 U.S.C. 154(b) by 69 days.

(21) Appl. No.: 14/678,525

(22) Filed: Apr. 3, 2015

(65) Prior Publication Data
US 2015/0283306 A1    Oct. 8, 2015

Related U.S. Application Data

(60) Provisional application No. 61/974,936, filed on Apr. 3, 2014.

(51) Int. Cl.
    A61F 13/00    (2006.01)
    A61L 31/04    (2006.01)
    A61L 31/14    (2006.01)
    A61L 31/18    (2006.01)

(52) U.S. Cl.
    CPC ........... *A61L 31/048* (2013.01); *A61L 31/145* (2013.01); *A61L 31/18* (2013.01); *A61L 2300/102* (2013.01); *A61L 2430/36* (2013.01)

(58) Field of Classification Search
    None
    See application file for complete search history.

(56) References Cited

U.S. PATENT DOCUMENTS

| | | |
|---|---|---|
| 3,709,842 A | 1/1973 | Stoy et al. |
| 3,749,085 A | 7/1973 | Wilson et al. |
| 4,020,829 A | 5/1977 | Wilson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |
| 4,663,358 A | 5/1987 | Hyon et al. |
| 4,795,741 A | 1/1989 | Leshchiner et al. |
| 4,819,637 A | 4/1989 | Dormandy, Jr. et al. |
| 4,932,419 A | 6/1990 | de Teledo |
| 4,951,677 A | 8/1990 | Crowley et al. |
| 4,994,069 A | 2/1991 | Ritchart et al. |
| 5,120,349 A | 6/1992 | Stewart et al. |
| 5,122,136 A | 6/1992 | Guglielmi et al. |
| 5,129,180 A | 7/1992 | Stewart |
| 5,133,731 A | 7/1992 | Butler et al. |
| 5,147,646 A | 9/1992 | Graham |
| 5,154,705 A | 10/1992 | Fleischhacker et al. |
| 5,163,952 A | 11/1992 | Froix |
| 5,165,421 A | 11/1992 | Fleischhacker et al. |
| 5,217,484 A | 6/1993 | Marks |
| 5,226,911 A | 7/1993 | Chee et al. |
| 5,258,042 A | 11/1993 | Mehta |
| 5,304,194 A | 4/1994 | Chee et al. |
| 5,312,415 A | 5/1994 | Palermo |
| 5,350,397 A | 9/1994 | Palermo et al. |
| 5,354,290 A | 10/1994 | Gross |
| 5,373,619 A | 12/1994 | Fleischhacker et al. |
| 5,382,259 A | 1/1995 | Phelps et al. |
| 5,382,260 A | 1/1995 | Dormandy, Jr. et al. |
| 5,443,478 A | 8/1995 | Purdy |
| 5,449,369 A | 9/1995 | Imran |
| 5,456,693 A | 10/1995 | Conston et al. |
| 5,469,867 A | 11/1995 | Schmitt |
| 5,476,472 A | 12/1995 | Dormandy, Jr. et al. |
| 5,483,022 A | 1/1996 | Mar |
| 5,522,822 A | 6/1996 | Phelps et al. |
| 5,525,334 A | 6/1996 | Ito et al. |
| 5,536,274 A | 7/1996 | Neuss |
| 5,541,234 A | 7/1996 | Unger et al. |
| 5,549,624 A | 8/1996 | Mirigian |
| 5,573,520 A | 11/1996 | Schwartz et al. |
| 5,573,994 A | 11/1996 | Kabra et al. |

(Continued)

FOREIGN PATENT DOCUMENTS

| | | |
|---|---|---|
| CA | 2551373 C | 6/2014 |
| CN | 102107025 B | 5/2014 |

(Continued)

OTHER PUBLICATIONS

Son et al., Preparation of properties of PEG-modified PHEMA hydrogel and the morphological effect. Macromolecular Research, vol. 14, No. 3, pp. 394-399 (2006).

Ahuja et al., Platinum coil coatings to increase thrombogenicity: a preliminary study in rabbits, AJNR, 14: 794-789 (1993).

Almany, Biomaterials, 26, 2005, 2467-2477, Biosynthetic hydrogel scaffolds made from fibrinogen and polyethylene glycol for 3D cell cultures.

Carelli V. et al., "Silicone microspheres for pH-controlled gastro-intestinal drug delivery," 1999, International Journal of Pharmaceutics, V179, p. 73-83.

Chirila et al., Poly(2-hydroxyethyl metharcrylate) sponges ans implant materials: in vivo and in vitro evaluation of cellular invasion. Biomaterials, 14(1):26-38 (1993).

Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).

(Continued)

*Primary Examiner* — James W Rogers
(74) *Attorney, Agent, or Firm* — K&L Gates LLP; Louis C. Cullman; Brian J. Novak

(57) ABSTRACT

Described herein are apparatus, compositions, systems and methods for occluding vascular structures and vascular malformations with radiopaque hydrogel filaments. The filaments can contain no support members and can be CT and MR compatible. Methods of forming such filaments are also disclosed.

12 Claims, 5 Drawing Sheets

(56) References Cited

U.S. PATENT DOCUMENTS

| | | |
|---|---|---|
| 5,578,074 A | 11/1996 | Mirigian |
| 5,580,568 A | 12/1996 | Greff et al. |
| 5,582,610 A | 12/1996 | Gross et al. |
| 5,582,619 A | 12/1996 | Ken |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A | 8/1997 | Snyder |
| 5,667,767 A | 9/1997 | Greff et al. |
| 5,672,634 A | 9/1997 | Tseng et al. |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,695,480 A | 12/1997 | Evans et al. |
| 5,702,361 A | 12/1997 | Evans et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,755,658 A | 5/1998 | Wallace et al. |
| 5,766,160 A | 6/1998 | Samson et al. |
| 5,766,219 A | 6/1998 | Horton |
| 5,823,198 A | 10/1998 | Jones et al. |
| 5,830,178 A | 11/1998 | Jones et al. |
| 5,843,743 A | 12/1998 | Hubbell et al. |
| 5,851,508 A | 12/1998 | Greff et al. |
| 5,853,419 A | 12/1998 | Ken et al. |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,004,573 A | 12/1999 | Rathi et al. |
| 6,013,084 A | 1/2000 | Ken et al. |
| 6,015,424 A | 1/2000 | Rosenbluth et al. |
| 6,017,977 A | 1/2000 | Evans et al. |
| 6,051,607 A | 4/2000 | Greff |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,146,373 A | 11/2000 | Cragg et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,187,024 B1 | 2/2001 | Boock et al. |
| 6,193,728 B1 | 2/2001 | Ken et al. |
| 6,201,065 B1 | 3/2001 | Pathak et al. |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,604 B1 | 10/2001 | Ragheb et al. |
| 6,299,619 B1 | 10/2001 | Greene, Jr. et al. |
| 6,299,627 B1 | 10/2001 | Eder et al. |
| 6,303,100 B1 | 10/2001 | Ricci et al. |
| 6,312,421 B1 | 11/2001 | Boock |
| 6,333,020 B1 | 12/2001 | Wallace et al. |
| 6,335,384 B1 | 1/2002 | Evans et al. |
| 6,342,202 B1 | 1/2002 | Evans et al. |
| 6,399,886 B1 | 6/2002 | Avellanet |
| 6,423,085 B1 | 7/2002 | Murayama et al. |
| 6,425,893 B1 | 7/2002 | Guglielmi et al. |
| 6,454,738 B1 | 9/2002 | Tran et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,537,569 B2 | 3/2003 | Cruise et al. |
| 6,558,367 B1 | 5/2003 | Cragg et al. |
| 6,565,551 B1 | 5/2003 | Jones et al. |
| 6,569,190 B2 | 5/2003 | Whalen et al. |
| 6,599,448 B1 | 7/2003 | Ehrhard, Jr. et al. |
| 6,602,261 B2 | 8/2003 | Greene, Jr. et al. |
| 6,605,294 B2 | 8/2003 | Sawhney |
| 6,623,450 B1 | 9/2003 | Dutta |
| 6,634,361 B1 | 10/2003 | Nikolchev et al. |
| 6,645,167 B1 | 11/2003 | Whalen et al. |
| 6,684,884 B2 | 2/2004 | Nikolchev et al. |
| 6,699,222 B1 | 3/2004 | Jones et al. |
| 6,723,108 B1 | 4/2004 | Jones et al. |
| 6,756,031 B2 | 6/2004 | Evans et al. |
| 6,759,028 B2 | 7/2004 | Wallace et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak et al. |
| 6,962,689 B2 | 11/2005 | Whalen et al. |
| 6,964,657 B2 | 11/2005 | Cragg et al. |
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,695,484 B2 | 4/2010 | Wallace et al. |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,172,862 B2 | 5/2012 | Wallace et al. |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,486,046 B2 | 7/2013 | Hayman et al. |
| 9,011,884 B2 | 4/2015 | Constant et al. |
| 2001/0023325 A1 | 9/2001 | Ferrera |
| 2002/0026234 A1 | 2/2002 | Li et al. |
| 2002/0042378 A1 | 4/2002 | Reich et al. |
| 2002/0169473 A1 | 11/2002 | Sepetka et al. |
| 2002/0176880 A1 | 11/2002 | Cruise et al. |
| 2003/0021762 A1 | 1/2003 | Luthra et al. |
| 2003/0077272 A1 | 4/2003 | Pathak et al. |
| 2003/0078339 A1 | 4/2003 | Kiser et al. |
| 2003/0086874 A1 | 5/2003 | Whalen, II et al. |
| 2003/0100942 A1 | 5/2003 | Ken et al. |
| 2003/0134032 A1 | 7/2003 | Chaouk et al. |
| 2003/0211083 A1 | 11/2003 | Vogel et al. |
| 2003/0220245 A1 | 11/2003 | Hubbell et al. |
| 2003/0232198 A1 | 12/2003 | Lamberti et al. |
| 2003/0232895 A1 | 12/2003 | Omidian et al. |
| 2004/0006534 A1 | 1/2004 | Schaefer et al. |
| 2004/0024098 A1 | 2/2004 | Mather et al. |
| 2004/0059370 A1 | 3/2004 | Greene et al. |
| 2004/0091543 A1 | 5/2004 | Bell et al. |
| 2004/0098028 A1 | 5/2004 | Martinez |
| 2004/0115164 A1 | 6/2004 | Pierce et al. |
| 2004/0158282 A1 | 8/2004 | Jones et al. |
| 2004/0209998 A1 | 10/2004 | De Vries |
| 2005/0003010 A1 | 1/2005 | Cohen et al. |
| 2005/0008610 A1 | 1/2005 | Schwarz et al. |
| 2005/0095428 A1 | 5/2005 | DiCarlo et al. |
| 2005/0106119 A1 | 5/2005 | Brandom et al. |
| 2005/0119687 A1 | 6/2005 | Dacey et al. |
| 2005/0143484 A1 | 6/2005 | Fang et al. |

(56) References Cited

U.S. PATENT DOCUMENTS

| | | |
|---|---|---|
| 2005/0171572 A1 | 8/2005 | Martinez et al. |
| 2005/0175709 A1 | 8/2005 | Baty et al. |
| 2005/0196426 A1 | 9/2005 | Cruise et al. |
| 2005/0196449 A1 | 9/2005 | DiCarlo et al. |
| 2005/0226935 A1 | 10/2005 | Kamath et al. |
| 2005/0281883 A1 | 12/2005 | Daniloff et al. |
| 2006/0052815 A1 | 3/2006 | Fitz et al. |
| 2006/0067883 A1 | 3/2006 | Krom et al. |
| 2006/0074370 A1 | 4/2006 | Zhou |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0202046 A1 | 8/2007 | Dave |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237720 A1 | 10/2007 | Padilla et al. |
| 2007/0237741 A1 | 10/2007 | Figuly et al. |
| 2007/0248567 A1 | 10/2007 | Pathak et al. |
| 2007/0254005 A1 | 11/2007 | Pathak et al. |
| 2007/0288084 A1 | 12/2007 | Lee et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0208167 A1 | 8/2008 | Stankus |
| 2008/0226741 A1 | 9/2008 | Richard |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0081275 A1 | 3/2009 | Rolfes et al. |
| 2009/0093550 A1 | 4/2009 | Rolfes et al. |
| 2009/0117033 A1 | 5/2009 | O'Gara |
| 2009/0164013 A1 | 6/2009 | Cruise et al. |
| 2009/0181068 A1 | 7/2009 | Dunn |
| 2009/0221731 A1 | 9/2009 | Vetrecin et al. |
| 2009/0232869 A1 | 9/2009 | Greene |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0086678 A1 | 4/2010 | Arthur et al. |
| 2010/0092533 A1 | 4/2010 | Stopek et al. |
| 2010/0241160 A1 | 9/2010 | Murphy |
| 2010/0247663 A1 | 9/2010 | Day et al. |
| 2010/0249913 A1 | 9/2010 | Datta et al. |
| 2010/0256777 A1 | 10/2010 | Datta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0091549 A1 | 4/2011 | Blaskovich et al. |
| 2011/0182998 A1 | 7/2011 | Reb et al. |
| 2011/0184455 A1 | 7/2011 | Keeley |
| 2011/0190813 A1 | 8/2011 | Brownlee et al. |
| 2011/0202016 A1 | 8/2011 | Zugates et al. |
| 2011/0212178 A1 | 9/2011 | Constant et al. |
| 2012/0041481 A1 | 2/2012 | Daniloff et al. |
| 2012/0083523 A1 | 4/2012 | Richard et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2012/0283769 A1 | 11/2012 | Cruise et al. |
| 2012/0289995 A1 | 11/2012 | Constant et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0131716 A1 | 5/2013 | Cruise et al. |
| 2013/0253087 A1 | 9/2013 | Cruise et al. |
| 2013/0302251 A1* | 11/2013 | Constant ............ A61K 49/0404 424/9.3 |
| 2014/0056806 A1 | 2/2014 | Vernengo et al. |
| 2014/0274945 A1 | 9/2014 | Blaskovich et al. |
| 2014/0277057 A1 | 9/2014 | Ortega et al. |
| 2015/0190553 A1 | 7/2015 | Constant et al. |
| 2015/0306227 A1 | 10/2015 | Cruise et al. |
| 2015/0306255 A1 | 10/2015 | Constant et al. |

FOREIGN PATENT DOCUMENTS

| | | |
|---|---|---|
| EP | 809519 B1 | 12/1997 |
| EP | 1599258 B1 | 8/2008 |
| EP | 1601392 B1 | 4/2009 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |
| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/147145 A2 | 12/2007 |
| WO | 2009/086208 A2 | 7/2009 |
| WO | 2011/038291 A1 | 3/2011 |
| WO | 2011/053555 A1 | 5/2011 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |

OTHER PUBLICATIONS

Edleman et al., Controlled and modulated release of basic fibroblast growth factor. Biomaterials, vol. 12, pp. 619-626 (1991).

Elbert et al., Conjugate addition reactions combined with free-radical cross-linking for the design of materials for tissue engineering. Biomacromolecules, (2): 430-441 (2001).

European Search Opinion for EP Application No. 10819570 dated Mar. 31, 2014.

European Search Opinion for EP Application No. 10827370 dated Apr. 1, 2014.

Graves et al., Endovascular occlusion of the carotid or vertebral artery with temporary proximal flow arrest and mircocoils: clinical results. AJNR Am. J. Neuroradiol., vol. 18, pp. 1201-1206 (1997).

Hoekstra, D., Hyaluronan-modified surfaces for medical devices. Medical Device & Diagnostic Industry, pp. 48-56 (1999).

Hogg et al., Interaction of platelet-derived growth factor with thrombospondin 1. Biochem. J. 326, pp. 709-716 (1997).

Horak et al., Hydrogels in endovascular embolization. II. Clinical use of spherical particles. Biomaterials, 7(6): 467-470 (1986).

Horak et al., New radiopaque polyHEMA-based hydrogel particles. J. Biomed. Matter Res., 34(2): 183-188 (1997).

Huang, et al., "Synthesis and Characterization of Self-Assembling Block Copolymers Containing Adhesive Molecules," Polymer Preprints, vol. 42, No. 2, 2001, pp. 147-148.

International Search Report dated on Dec. 17, 2010 for International Patent Application No. PCT/US2010/053972.

International Search Report dated Feb. 5, 2009 for International Patent Application No. PCT/US2007/071395.

(56) References Cited

OTHER PUBLICATIONS

International Search Report dated Aug. 14, 2013 for International PCT Application No. PCT/US2013/037007 filed on Apr. 17, 2013.
International Search Report and Written Opinion dated Jun. 29, 2015 for International Application No. PCT/US2015/024289 filed on Apr. 3, 2015.
International Search Report and Written Opinion dated Jun. 29, 2015 for International Application No. PCT/US2015/024290 filed on Apr. 3, 2015.
International Search Report and Written Opinion dated Jul. 14, 2015 for International Application No. PCT/US2015/024284 filed on Apr. 3, 2015.
Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.
Klier, Self Associating Networks of Poly(methacrylic acid g-ethylene glycol) Marcomolecules 1990, vol. 23, 1990, p. 4944-4949.
Larsen et al., Hylan gel composition for percutaneous embolization. Journal of Biomedical Materials Research, vol. 25, Issue 6, pp. 699-710 (1991).
Latchaw et al., Polyvinyl foam embolization of vascular and neoplastic lesions of the head, neck, and spine. Radiology, 131: 669-679 (1979).
Li, Jian et al., Preparation of PEG/Aac copolymerric hydrogel and study of pH-sensitivity. Chemistry World, Issue 1, pp. 20-23 (2005).
Mellott, Michael B. et al., Release of protein from highly cross-linked hydrogels of poly(ethylene glycol) diacrylate fabricated by UV polymerization. Biomaterials, 22(2001) 929-941.
Murayama et al., Cellular responses of bioabsorbable polymeric material and guglielmi detachable coil in experimental aneurysms. Stroke, pp. 1120-1128 (2002).
Persidis, A., Tissue engineering. Nature Biotechnology, 17, pp. 508-510 (1999).
Schmutz et al., Embolization of cerebral arteriovenous malformations with silk: histopathologic changes and hemorrhagic complications. AJNR Am. J. Neuroradiol., vol. 18, pp. 1233-1237 (1997).
Schoenmakers, The effect of the linker on the hydrolysis rate of drug-linked ester bonds, J. Cont. Rel., 95, 2004, pp. 291-300.
Supplementary European Search Report for EP Application No. 10819570 dated Mar. 31, 2014.
Supplementary European Search Report for EP Application No. 10827370 dated Apr. 1, 2014.
Vinlela et al., Guglielmi detachable coil embolization of acute intracranial aneurysm: perioperative anatomical and clinical outcome in 403 patients. J. Neurosurg., vol. 86, pp. 475-482 (1997).
Woerly et al., Intracerebral implantation of hydrogel-coupled adhesion peptides: tissue reaction. Journal of Neural Transplantation & Plasticity, vol. 5, No. 4, pp. 245-255 (1995).
Written Opinion dated Aug. 14, 2013 for International PCT Application No. PCT/US2013/037007 filed on Apr. 17, 2013.
Zollikofer et al., A combination of stainless steel coil and compressed ivalon: a new technique for embolization of larger arteries and arteriovenous fistulas. Radiology, 138: 229-231 (1981).
Zollikofer et al., Therapeutic blockade of arteries using compressed invalon. Radiology, 136: 635-640 (1980).
U.S. Appl. No. 14/678,468, filed Apr. 3, 2015.
U.S. Appl. No. 14/678,514, filed Apr. 3, 2015.
International PCT Application PCT/US2015/024289 filed on Apr. 3, 2015.
International PCT Application PCT/US2015/024290 filed on Apr. 3, 2015.
International PCT Application PCT/US2015/024284 filed on Apr. 3, 2015.

* cited by examiner

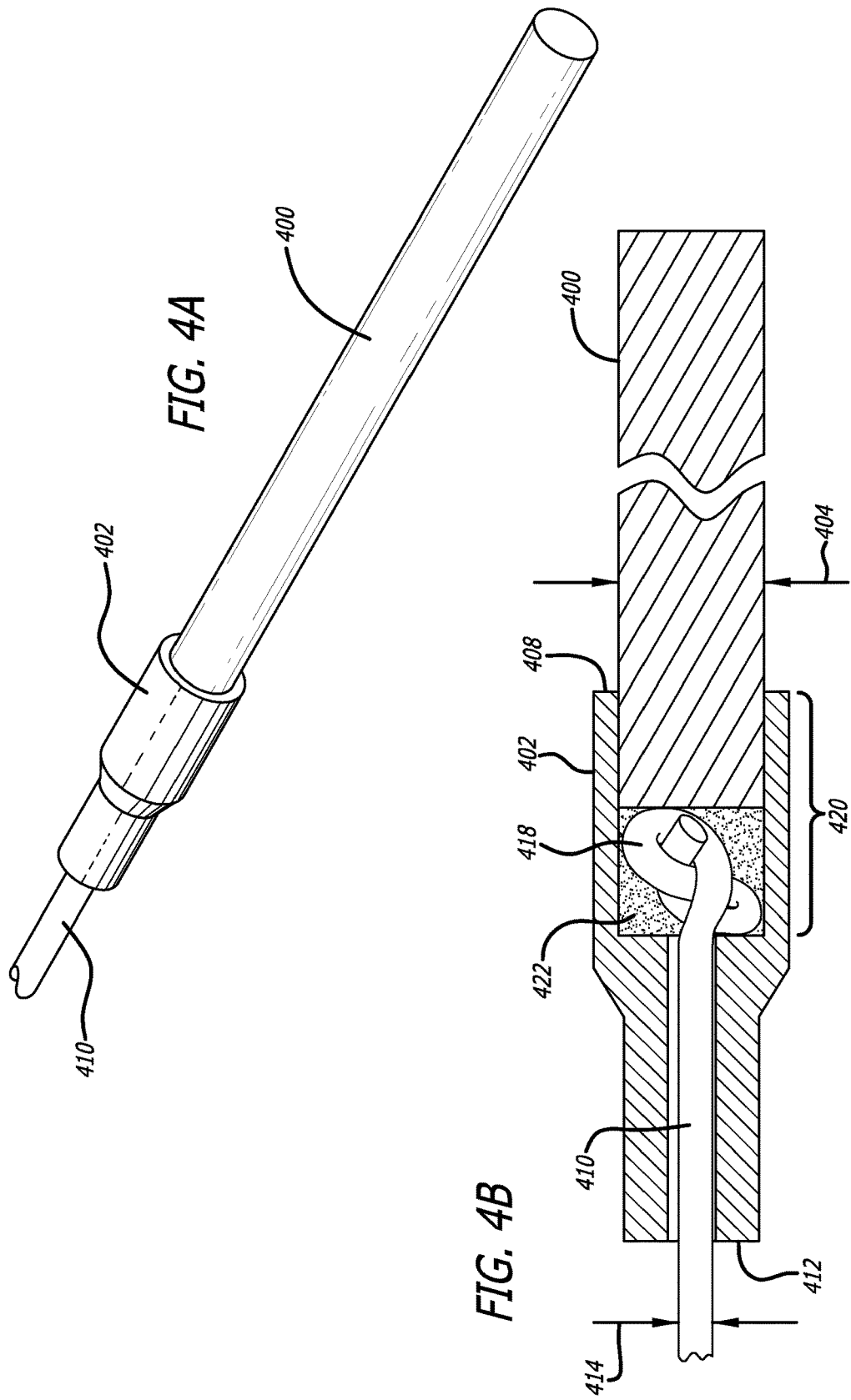

EMBOLIC DEVICES

CROSS REFERENCE TO RELATED APPLICATIONS

This application claims the benefit of U.S. Provisional Patent Application No. 61/974,936, filed Apr. 3, 2014, the entire disclosure of which is incorporated herein by reference.

FIELD

The present invention relates generally to implantable hydrogel filaments and medical treatment methods using the hydrogel filaments, wherein the filaments can be visualized using medically relevant imaging techniques.

BACKGROUND

Despite the number of vascular coil devices available, there exists a clinical need for polymer filament devices that can be deployed using standard microcatheters and catheters to treat sites in the peripheral vasculature. Of particular clinical need is a polymer filament device that can be deployed using standard medical techniques through standard microcatheters and catheters to treat sites in the neuro and peripheral vasculature and can be compatible with various medical imaging techniques such as computed tomography imaging.

SUMMARY

Described herein generally are hydrogels and hydrogel filaments, methods of forming those hydrogels and hydrogel filaments, and medical treatment methods using the hydrogels and hydrogel filaments. The hydrogel filaments possess enough structural strength not to require support members such as metallic support members when deployed in vivo through a vessel. The filaments can also be opacified in order to visualize the filaments using medically relevant imaging techniques.

In one embodiment, hydrogels are described for implantation comprising a shapeable polymeric filament formed from a reaction product of at least one multifunctional, low molecular weight, ethylenically unsaturated macromer; at least one ethylenically unsaturated monomer; and comprising at least one visualization element. The polymeric filament may include no metallic support members. In some embodiments, the hydrogels can be further formed with an ethylenically unsaturated cross-linker, which can be multifunctional.

In another embodiment, hydrogels for implantation are described comprising a shapeable polymeric filament formed from a combination of precursors comprising at least one low molecular weight, ethylenically unsaturated macromer; at least one ethylenically unsaturated monomer; and a crosslinker. The hydrogels can comprise at least one visualization agent; and wherein the hydrogel includes no metal support members.

In some embodiments, the at least one ethylenically unsaturated monomer can be t-butyl acrylamide, hydroxyethyl methacrylate, or a combination of both. The macromer can be a difunctional, trifunctional, or have further degrees of functionality. In one embodiment, the macromer can be trifunctional. A multifunctional macromer can be trimethylolpropane ethoxylate triacrylamide and may have a molecular weight of about 900 g/mol. In some embodiments, the crosslinker can be N,N'-methylenebisacrylamide.

In other embodiments, the hydrogels can reduce beam hardening artifacts when imaged using computed tomography. A visualization element can be a soluble or insoluble opacification compound, gadolinium, iodine, barium sulfate, superparamagnetic iron oxide particles, or a combination thereof. In another embodiment, a visualization element can be barium sulfate. For example, barium sulfate can be useful for fluoroscopic and CT visibility. For MR visibility, the filaments can be opacified with gadolinium or superparamagnetic iron oxide particles.

Polymer filaments can be sized with virtually any diameter. In some embodiments, polymer filaments can be sized to deploy, and optionally reposition, through microcatheters with inner diameters ranging from about 0.002 inches to about 0.045 inches. In another embodiment, polymer filaments can be sized to deploy, and optionally reposition, through 2 Fr, 3 Fr, 4 Fr, 5 Fr, 6 Fr, 7 Fr, 8 Fr, 9 Fr, 10 Fr, and larger catheters. The polymer filaments generally can have diameters of greater than about 0.002 inches or less than about 0.100 inches.

In one embodiment, polymer filaments can be delivered with a saline flush through a microcatheter or catheter to the vasculature. In another embodiment, polymer filaments can be delivered using a guide wire or coil pusher through the microcatheter or catheter to the vasculature. In some embodiments, polymer filaments can be releasably attached to a delivery pusher. After repositioning, if desired, polymer filaments can be detached from the delivery pusher and the delivery pusher can be subsequently removed.

In one embodiment, polymer filaments can be biostable and not susceptible to degradation or any substantial degradation in a physiological environment. Alternatively in another embodiment, polymer filaments can be biodegradable and controllably dissolve in a physiological environment.

In one embodiment, significant fluid uptake by a polymer filament may occur and a large increase in the volume of the polymer filament may occur in a physiological environment. In another embodiment, only a small amount of fluid uptake by a polymer filament may occur and only a small increase in the volume of the polymer filament may occur in a physiological environment. In yet another environment, no fluid uptake by a polymer filament may occur and the volume of the polymer filament may remain unchanged in a physiological environment.

Also described herein are methods of forming hydrogels comprising: a. preparing a polymerization solution comprising a trimethylolpropane ethoxylate triacrylamide 900 macromer; at least one ethylenically unsaturated monomer; and at least one visualization element in a solvent; b. polymerizing the polymerization solution to create a polymerized hydrogel; and c. drying the hydrogel filament. In another embodiment, step b can further comprise polymerizing the polymerization solution in a tube thereby creating a polymerized hydrogel filament having the shape of the internal volume of the tube. In another embodiment, the tube may be wrapped around a mandrel of virtually any shape before filling with the polymerization solution to impart a three dimensional shape to the resulting polymerized hydrogel filament.

The solvent can be any solvent or combination or mixture of solvents that dissolves or substantially dissolves the macromers and monomers. In one embodiment, isopropanol, ethanol, water, dichloromethane, dimethyl formamide, acetone, butanol, or a combination thereof can be used as a solvent.

In some embodiments, hydrogel filaments can consist essentially of about 27% w/w trimethylolpropane ethoxylate triacrylamide 900, about 8% w/w t-butyl acrylamide, about 2% hydroxyethyl methacrylate, about 1% w/w N,N-methylenebisacrylamide, about 66% barium sulfate, and about <1% 2,2'-azobisisobutyronitrile.

In some embodiments, hydrogel filaments can consist essentially of about 30% w/w trimethylolpropane ethoxylate triacrylamide 900, about 6% w/w t-butyl acrylamide, about 2% hydroxyethyl methacrylate, about 1% w/w N,N-methylenebisacrylamide, about 61% barium sulfate, and about <1% 2,2'-azobisisobutyronitrile.

In one embodiment, an overcoil used with an embolic coil is described. The overcoil may aid in tracking the embolic coil through the delivery device.

In one embodiment, an embolic coil utilizes an overcoil. The overcoil may aid in tracking the embolic coil through the delivery device.

BRIEF DESCRIPTION OF THE DRAWINGS

FIG. 4A illustrates a hydrogel filament attached to a coupler. FIG. 4B illustrates a hydrogel filament and an insertion filament attached to a coupler using glue and a knot in the insertion filament.

DETAILED DESCRIPTION

Figure 1:
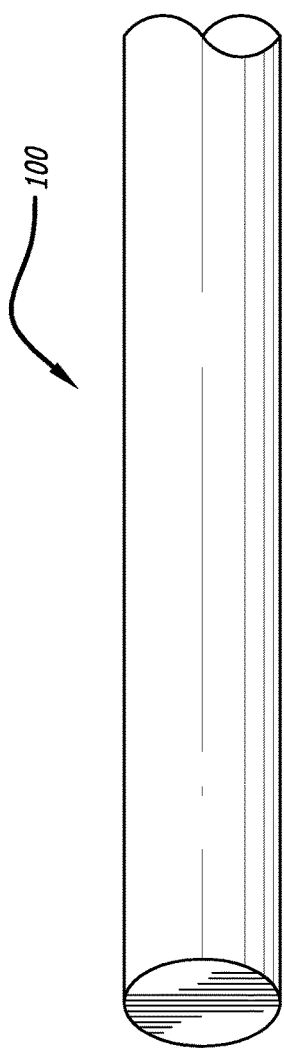
FIG. 1 illustrates a cylindrical hydrogel filament according to an embodiment of the present description.

Described herein generally are hydrogels and hydrogel filaments and medical treatment devices and methods using the hydrogels and hydrogel filaments. Methods of forming the hydrogel filaments are also described herein, including methods of making the hydrogel filaments. Generally, the hydrogel filaments can possess enough structural column strength so as to not require metallic support members. The filaments can also be opacified in order to visualize the filaments using medically relevant imaging techniques.

The hydrogel filaments and associated methods can be used for occluding structures and malformations resulting from one or more neuro, cerebral and/or peripheral vascular diseases. Further, the hydrogel filaments include one or more visualization agents, for example, radiopaque elements or fillers.

Generally, the hydrogel filaments can be deployed within the vasculature using standard practices and microcatheters/catheters to occlude blood flow. The polymer filaments can be prepared by polymerizing a solution of monomers, macromers, and optionally, cross-linkers. For fluoroscopic visibility, the filaments can be opacified with any compound or substance that can be used to visualize the filaments. For example, the filaments can be opacified with iodine, barium sulfate, or metallic powders. For computed tomography imaging, the filaments can be opacified with iodine or barium sulfate. For magnetic resonance imaging, the filaments can be opacified with gadolinium or superparamagnetic iron oxide particles.

As used herein, the term "macromer" includes large molecules containing at least one active polymerization site or binding site. Macromers can have a larger molecular weight than monomers such as at least about 100 grams/mole, about 200 grams/mole, about 500 grams/mole or about 900 grams/mole. For example, an acrylamide monomer can have a molecular weight of about 71.08 grams/mole whereas a trimethylolpropane ethoxylate triacrylamide macromer can have a molecular weight of about 900 grams/mole. Some macromers can be shapeable and non-ionic.

As used herein, the term "non-resorbable" includes a material that cannot be readily and/or substantially degraded and/or absorbed by bodily tissues.

As used herein, the term "ethylenically unsaturated" includes a chemical entity (e.g., a macromer, monomer or polymer) containing at least one carbon-carbon double bond.

Some hydrogel filaments described herein may have no metal support members to aid in supporting the filaments before, during and after implantation. The filaments can be delivered through a catheter or microcatheter using a pusher or guidewire or even a liquid flush (e.g. saline). The hydrogel filaments may have sufficient column strength to alleviate the need for metal support member, yet soft and flexible enough to navigate through vasculature. However, unlike filaments in the art, the hydrogel filaments described herein can have sufficient column strength to be advanced out of a catheter or microcatheter device by pushing with a pusher or guidewire.

Filaments described herein can be shapeable in that they can be formed into a particular shape and hold that shape for a predetermined amount of time once hydrated. For example, the time can be about 10 seconds, about 30 seconds, about 1 minute, about 5 minutes, about 15 minutes, about 30 minutes, about 1 hour, between about 10 seconds and about 5 minutes, between about 10 seconds and about 1 min, between about 30 seconds and about 30 minutes, or between about 5 minutes and about 15 min. For example the filaments described herein can be formed around a mandrel or wrapped around one once formed to establish a secondary shape for the filament.

Filaments described herein may be formed from polymerization solutions comprising such components as one or more solvent(s), one or more macromer(s), one or more monomer(s), one or more cross-linker(s), one or more visualization agent(s), and one or more initiator(s). Some components may be optional.

The solvent's function can be to dissolve at least part of the macromers, monomers, cross-linkers, initiators, and soluble visualization agents needed to form a particular filament. In some instances, all of the components may be completely dissolved in the solvent. In other embodiments, the visualization agent or agents may or may not dissolve in the solvent. If a liquid monomer (e.g. 2-hydroxyethyl methacrylate) is used, a solvent may not be necessary. The solvent, if necessary, can be selected based on the solubility of the components of the polymerization solution. Solvents can include isopropanol, ethanol, water, dichloromethane, dimethyl formamide, butanol, and acetone. Any number of solvents can be utilized and a skilled artisan can match a solvent to a particular polymer system.

Solvent concentrations can be from about 5% w/w to about 80% w/w, about 30% w/w to about 60% w/w, about 40% w/w to about 50% w/w, about 5% w/w, about 10% w/w, 20% w/w, 30% w/w, 40% w/w, 50% w/w, 60% w/w, 70% w/w, 80% w/w, 90% w/w of the polymerization solution, or any percentage or range of percentages within those listed. In one embodiment, the solvent can make up about 15% w/w of the polymerization solution.

The polymerization solutions may include at least one macromer. A function of the macromer can be to impart desired mechanical properties to the filaments as well as provide a bulk structural framework for the filament. Macromers with solubility in solvents and functional groups amenable to modifications can be used in some embodiments. Polyethers, due to their solubility in a variety of solvents, their availability in a variety of forms, and their terminal groups amenable to functionalization, can be utilized herein. While poly(ethylene glycol), poly(propylene glycol), and poly(tetramethylene oxide) can be suitable polyethers, a preferred macromer can be ethoxylated trimethylolpropane having a low molecular weight and the presence of three hydroxyl groups. Non-polyether polymers with functional groups available for modification, such as poly(vinyl alcohol), can also be utilized as macromers. In one embodiment, the macromer may be trimethylolpropane ethoxylate triacrylamide. In another embodiment the macromer can be ethoxylated trimethylolpropane triacrylamide with a molecular weight of about 900 g/mole.

Macromer concentrations can range from about 10% w/w to about 40% w/w, about 20% w/w to about 35% w/w, about 12% w/w to about 20% w/w, about 22% w/w to about 24% w/w, or any percentage or range of percentages within those listed of the polymerization solution. In one embodiment, the macromer concentration can be about 23% w/w or about 25% w/w of the polymerization solution.

The molecular weight of the macromer can change the resulting hydrogel's mechanical properties, in some cases to a large extent. Smaller molecular weights can result in filaments with sufficient column strength to be pushed through microcatheters and catheters. Larger molecular weights may result in filaments that can require more effort to be pushed through microcatheters and catheters. The macromers described herein can have a molecular weight of about 400 g/mole, about 500 g/mole, about 600 g/mole, about 700 g/mole, about 800 g/mole, about 900 g/mole, about 1,000 g/mole, about 1,100 g/mole, about 1,200 g/mole, about 1,300 g/mole, about 1,400 g/mole, about 1,500 g/mole, about 1,600 g/mole, about 1,800 g/mole, about 2,000 g/mole, about 2,500 g/mole, or about 5,000 g/mole or ranging from about 100 g/mole to about 5,000 g/mole, about 250 g/mole to about 2,500 g/mole, about 400 g/mole to about 1,200 g/mole, about 100 g/mole to about 400 g/mole, about 250 g/mole to about 400 g/mole, about 2,500 g/mole to about 5,000 g/mole, about 1,200 g/mole to about 2,500 g/mole, or any molecular weight or range of molecular weights within those listed. In one embodiment, molecular weight can be about 900 g/mole.

Any functional groups associated with the macromers described can be derivatized. The functional groups of the macromers can be derivatized to impart ethylenically unsaturated moieties allowing free radical polymerization of the hydrogel. Functionalities for free radical polymerization can include acrylates, methacrylates, acrylamides, vinyl groups, derivatives and/or combinations thereof. Alternatively, other reactive chemistries can be employed to polymerize the hydrogel, for example, nucleophile/N-hydroxysuccinimde esters, vinyl sulfone/acrylate or maleimide/acrylate. In one embodiment, a preferred functional group of the macromer can be an acrylate.

Biostability, non restorability, and/or biodegradation can be imparted to hydrogels described by altering the synthetic route to derivatize macromer functional groups. If biostability and/or non restorability are desired, a linkage with stability in the physiological environment can be utilized. The biostable linkage can be an amide. The macromer hydroxyl group(s) can be converted to an amino group followed by reaction with acryloyl chloride to form an acrylamide group. If biodegradation is desired, linkages susceptible to breakage in a physiological environment can be utilized. Biodegradable linkages can include esters, polyesters, and amino acid sequences degradable by enzymes.

Monomers can also be used to aid in polymerization of the hydrogel and impart specific mechanical properties to the resulting hydrogel. In one embodiment, the monomers may not be sensitive to pH. The monomers can be any molecule with a single functionality to incorporate into the resulting hydrogel and a structure conducive to the desired mechanical property. The monomers can be, for example, hydrophobic thereby imparting column strength to the resulting hydrogel. Also or in addition, the monomer can have a bulky structure further imparting column strength to the resulting hydrogel. Internal hydrogen bonding within the monomer can impart increasing tensile strength to the resulting polymer. Monomers can include t-butyl acrylamide, 2-hydroxyethyl methacrylate, and derivatives thereof. Concentrations of monomers can range from about 2% to about 30% w/w, about 3% w/w to about 12% w/w about 5% w/w to about 10% w/w of the polymerization solution, or any percentage or range of percentages within those listed. In some embodiments, the monomer can be t-butyl acrylamide and can be present at about 5% w/w or about 6% w/w. In some embodiments the monomer can be hydroxyethyl methacrylate and can be present at about 2% w/w. In other embodiments, the monomer can be a combination of t-butyl acrylamide and hydroxyethyl methacrylate.

In one embodiment, depending on the monomers chosen for a particular hydrogel, significant fluid uptake by the polymer filament can occur and a large increase in the volume of the polymer filaments can occur in a physiological environment. In another embodiment, monomers chosen may allow only a small amount of fluid uptake by the polymer filament and only a small increase in the volume of the polymer filament may occur in a physiological environment. In yet another environment, monomers chosen can prevent fluid uptake by the polymer filament and the volume of the polymer filaments can remain unchanged in a physiological environment.

Crosslinker(s), although optional, can impart desired mechanical properties to the hydrogels. The crosslinker can be a multifunctional crosslinker. The crosslinker can be any molecule with at least two functionalities to incorporate into the resulting hydrogel and a structure conducive to the desired mechanical property. One example crosslinker can be N,N-methylenebisacrylamide. Concentrations of the crosslinker can be less than about 2% w/w, less than about 1% w/w, less than about 0.5% w/w, or less than about 0.1% w/w of the polymerization solution. In some embodiments, the concentration of the crosslinker is about 0.2% w/w, about 0.5% w/w, about 1% w/w, or about 2% w/w. The crosslinker can be at any percentage or range of percentages within those listed. In one embodiment, the concentration of crosslinker can be about 0.5% w/w.

In one embodiment, polymerization can be initiated by azobisisobutyronitrile (AIBN) or a water soluble AIBN derivative. In one embodiment, a water soluble AIBN derivative can be 2,2'-azobis(2-methylpropionamidine)dihydrochloride. Other initiators useful according to the present description include N,N,N',N'-tetramethylethylenediamine, ammonium persulfate, benzoyl peroxides, 2,2'-azobis(2-methylpropionamidine)dihydrochloride, and derivatives and/or combinations thereof, including azobisisobutyronitriles. Azobisisobutyronitrile can be the initiator. Concentrations of the initiator can be less than about 5% w/w or about 1% w/w of the prepolymer solution.

A function of the initiator may be to start the polymerization of the polymerizable components of the prepolymer or polymerization solution. The prepolymer solution can be polymerized by reduction-oxidation, radiation, heat, or any other method known in the art. Radiation cross-linking of the pre-polymer solution can be achieved with ultraviolet light or visible light with suitable initiators or ionizing radiation (for example, electron beam or gamma ray) without initiators. Cross-linking can be achieved by application of heat, either by conventionally heating the solution using a heat source such as a heating well, or by application of infrared light to the prepolymer solution.

Visualization agents can also be added to the hydrogels described herein. Since metallic support members are not used in conjunction with the presently described hydrogel filaments, visualization agents can be added to the hydrogels to impart visualization. Generally, in the art, metallic support members aid in the visualization of embolic devices. Here, this is not the case. The visualization agents impart visibility of the resulting hydrogel when imaged using a medically relevant imaging technique such as fluoroscopy, computed tomography, or magnetic resonance techniques. However, in some embodiments, metallic support members can be used at least in or on portions of the hydrogel filament.

Visualization of the hydrogel filaments under fluoroscopy can be imparted by the incorporation of solid particles of radiopaque materials including barium, bismuth, tantalum, platinum, gold, and other heavy nuclei species into the hydrogel or by polymerization of iodine or other molecules or atoms into the hydrogel structure. For example, iodine or another molecule or atom can be incorporated into a monomer that is polymerized into the resulting hydrogel. Some embodiments include one, two, three, four, five or more iodine atoms or other atoms per monomeric unit added to the resulting hydrogel. A preferred visualization agent for fluoroscopy can be barium sulfate. Visualization of the hydrogel filaments under computed tomography imaging can be imparted by incorporation of solid particles of barium or bismuth.

Heavy metals visible under fluoroscopy can sometimes result in beam hardening artifacts that preclude the usefulness of computed tomography imaging for medical purposes. A visualization agent for computed tomography imaging may be barium sulfate. Concentrations of barium sulfate may range from about 30% w/w to about 90% w/w, about 40% w/w to about 80% w/w, about 60% w/w to about 70% w/w of the polymerization solution or any percentage or range of percentages within those listed. In one embodiment, barium sulfate can be present at about 50% w/w to about 60% w/w. Such concentrations of barium sulfate can render the hydrogel filaments visible using fluoroscopic and computed tomography imaging.

Visualization of the hydrogel under magnetic resonance imaging can be imparted by the incorporation of solid particles of superparamagnetic iron oxide or gadolinium molecules polymerized into the hydrogel structure. A visualization agent for magnetic resonance may be superparamagnetic iron oxide with a particle size of about 10 microns. Concentrations of superparamagnetic iron oxide particles to render the hydrogel visible using magnetic resonance imaging can range from about 0.01% w/w to about 2% w/w, about 0.05% w/w to about 0.75% w/w, about 0.1% w/w to about 1% w/w of the polymerization solution or any percentage or range of percentages within those listed.

In one embodiment, a hydrogel filament can be formed from a prepolymer solution containing or including a macromer, monomers, a crosslinker, an initiator and a visualization agent. In another embodiment, the macromer, monomers, crosslinker, and initiator can be dissolved in a solvent. After dissolution of these components, an insoluble visualization agent can be suspended in the prepolymer solution. Mixing of the prepolymer solution containing an insoluble visualization agent with a homogenizer may aid the suspension of the insoluble visualization agent.

Other embodiments form the hydrogel filament from a prepolymer solution containing or including a macromer, a monomer including a visualization agent, and an initiator. Still other embodiments form the hydrogel filament from a prepolymer solution containing or including a macromer, a visualization agent, and an initiator. Still other embodiments form the hydrogel filament from a prepolymer solution containing or including a macromer, a visualization agent, a crosslinker, and an initiator. In some embodiments, an initiator may not be needed.

In one embodiment, a hydrogel filament formed from an above prepolymer solution can include about 27% w/w trimethylolpropane ethoxylate triacrylamide 900, about 6% w/w t-butyl acrylamide, about 2% hydroxyethyl methacrylate, about 0.5% w/w N,N-methylenebisacrylamide, about 64% barium sulfate, and less than about 0.5% azobisisobutyronitrile.

In another embodiment, a hydrogel filament formed from an above prepolymer solution can include about 30% w/w trimethylolpropane ethoxylate triacrylamide 900, about 6% w/w t-butyl acrylamide, about 2% hydroxyethyl methacrylate, about 0.75% w/w N,N-methylenebisacrylamide, about 48% barium sulfate, and less than about 0.5% azobisisobutyronitrile.

The hydrogel filaments can have many characteristic properties one of which is bending resistance. Bending resistance can be based on factors such as diameter and/or hydration. The filaments can have a dry bending resistance of about 0.5 mg to about 1000 mg, about 1 mg to about 500 mg, about 2 mg to about 250 mg, about 5 mg to about 500 mg, about 10 mg to about 100 mg, about 0.49 mg, about 1.11 mg, about 6.67 mg, about 9.04 mg, about 10.56 mg, about 19.07 mg, about 36.39 mg, about 63.68 mg, about 128.21 mg, about 1,021.20 mg, or any bending resistance or range of bending resistances within those listed. The filaments can also have a hydrated bending resistance of about 0.5 mg to about 1000 mg, about 1 mg to about 500 mg, about 2 mg to about 250 mg, about 5 mg to about 500 mg, about 10 mg to about 100 mg, about 0.28 mg, about 4.73 mg, about 7.78 mg, about 8.62 mg, about 17.38 mg, about 29.40 mg, about 59.10 mg, about 121.58 mg, about 860.25 mg, or any bending resistance or range of bending resistances within those listed Another filament characteristic can be average ultimate tensile strength. The hydrogel filaments described herein can have an average ultimate tensile strength of about 0.03 lbf to about 2 lbf, about 0.08 lbf to about 0.20 lbf, about 0.52 lbf to about 0.65 lbf, about 0.1 lbf to about 10 lbf, about 1 lbf to about 15 lbf, about 0.05 lbf to about 20 lbf, about 0.07 lbf to about 2 lbf, about 0.03 lbf to about 0.1 lbf or any average ultimate tensile strength or range of average ultimate tensile strengths within those listed.

Methods of preparing hydrogels and/or hydrogel filaments are also described. The prepolymer solution can be prepared by dissolving at least one macromer, at least one monomer, optionally a multifunctional cross-linker, and optionally an initiator in a solvent, and adding a visualization agent to the prepolymer solution. A visualization agent can be suspended in the polymerization solution or can be dissolved in the prepolymer solution. In other embodiments, the visualization agent can be soluble in the solvent. Mixing of the polymerization solution containing an insoluble visualization agent with a homogenizer aids in suspension of the insoluble visualization agent.

Then, the polymerization solution can be injected into tubing with an inner diameter ranging from about 0.006 inches to about 0.080 inches and incubated for several hours in boiling water, for example, at 100° C., and subsequently overnight at 80° C. The immersion in boiling water can allow for rapid heat transfer from the water to the polymerization solution contained in the tubing. The selection of the tubing can impart microcatheter or catheter compatibility.

In some embodiments, polymer filaments can be sized to deploy, and optionally reposition, through microcatheters with inner diameters ranging from about 0.006 inches to about 0.045 inches or from about 0.006 inches to about 0.028 inches. In another embodiment, polymer filaments can be sized to deploy, and optionally reposition, through 2 Fr, 3 Fr, 4 Fr, 5 Fr, 6 Fr, 7 Fr, 8 Fr, 9 Fr, 10 Fr, and larger catheters.

Figure 2:
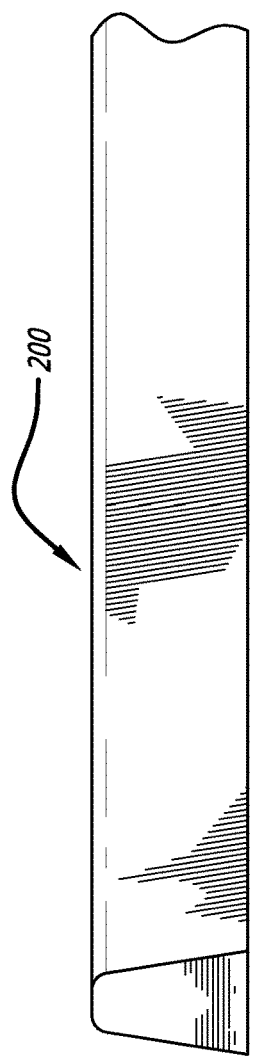
FIG. 2 illustrates a trapezoidal hydrogel filament according to an embodiment of the present description.
Figure 3:
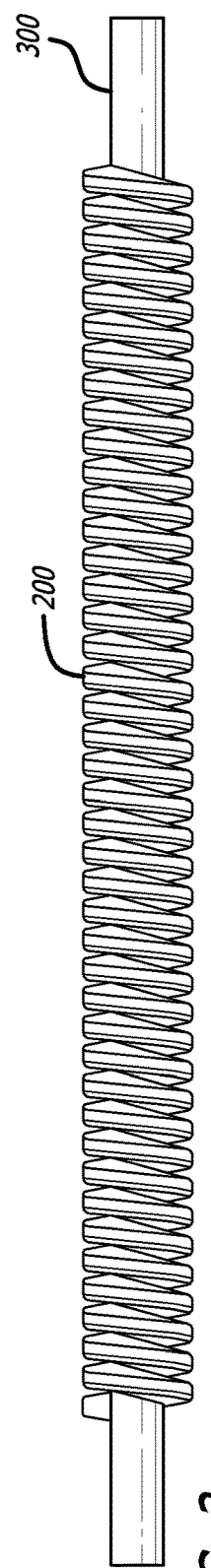
FIG. 3 illustrates the hydrogel filament of FIG. 2 wrapped around a mandrel to form a coil.

For delivery through some microcatheters, tubing diameters can range from about 0.006 inches to about 0.025 inches. For delivery through some 4 Fr, 5 Fr, 6 Fr, 7 Fr, and 8 Fr catheters, tubing diameters from about 0.025 inches to about 0.080 inches can be utilized. In one embodiment, the tubing may be made from HYTREL® (DuPont, Wilmington, Del.). The HYTREL® tubing can be dissolved in and/or by solvents, facilitating removal of the tube around the polymer hydrogel. Some hydrogel filament shapes are illustrated in FIGS. 1 and 2. FIG. 1 illustrates a cylindrical, circular or round filament 100 in a dried, straight state or configuration. FIG. 2 illustrates trapezoidal filament 200 in a dried, straight state or configuration FIG. 3 illustrates one method of how a hydrogel coil can be attained. If filament 200 is wrapped around a mandrel 300 prior to polymerization of the polymerization solution, the resulting polymer can maintain the shape of filament 200 around mandrel 300 or at least retain a memory of the shape. Using this technique, helical, tornado, and complex shapes can be imparted to the hydrogel filament. When the tubing is wrapped around a mandrel, the use of trapezoidal or oval tubing may be preferred. After wrapping around the mandrel, the oval shape of the tubing can be rounded and the resulting hydrogel filament can have a round shape.

Using HYTREL® tubing, the hydrogel filament can be recovered by incubating the tubing in a solution of 20% w/w phenol in chloroform followed by washing in chloroform and ethanol. After the hydrogel filament has been washed, it can be dried, and a dried hydrogel filament may be produced. The length of a dried filament can range from about 0.01 cm to about 1,000 cm, about 0.1 cm to about 500 cm, about 0.25 cm to about 250 cm, about 0.5 cm to about 100 cm, or any length or range of lengths within those listed. The diameter of a filament can range from about 0.002 inches to about 0.1 inches, 0.05 inches to about 0.1 inches, or any diameter within this range.

Once a filament has been synthesized and treated to produce the desired properties it can be loaded into an introducer device that facilitates clinical use. If a repositionable device is desired, a length of filament may be inserted into a tube slightly larger its diameter. This can straighten the secondary shape of the filament.

Figure 5A:
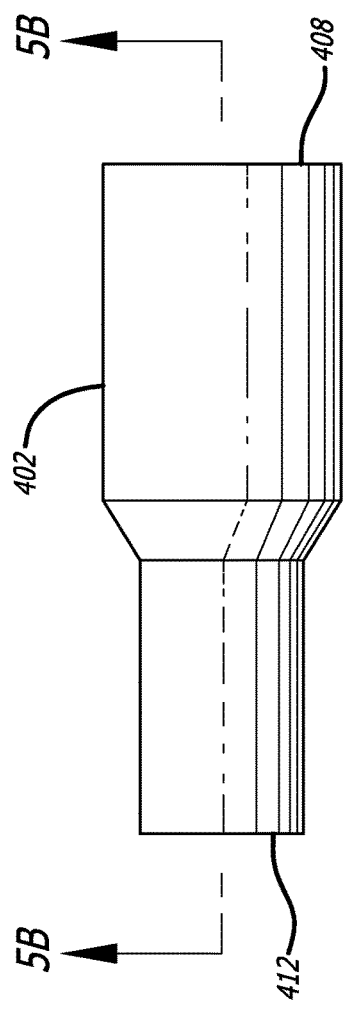
FIG. 5A illustrates a side view of a coupler.
Figure 5B:
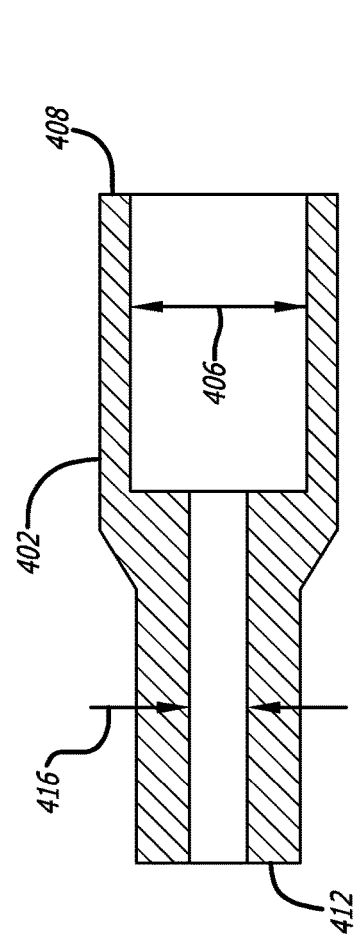
FIG. 5B illustrates a cross-sectional view of the coupler of FIG. 5A.
Figure 5C:
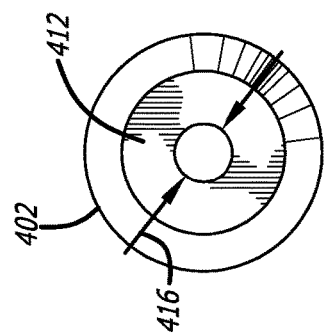
FIG. 5C is a front view of a coupler.

Further, as illustrated in FIGS. 4A and 4B, filament 400 can be attached to a coupler 402. Coupler 402 is further illustrated in various views in FIGS. 5A-5C. As is illustrated in FIG. 4B, the outer diameter 404 of filament 400 can be slightly smaller than or about the same size as the inner diameter 406 of first end 408 of coupler 402.

Coupler 402 can be further attached to an insertion filament 410 that is attached to second end 412 of coupler 402. Again, the outer diameter 414 of insertion filament 410 can be slightly smaller than or about the same size as the inner diameter 416 of second end 412 of coupler 402. Insertion filament 410 can be attached to coupler 402 by gluing, soldering, smashing, flaring, knotting or the like or a combination thereof. For example, as illustrated in FIG. 4B, insertion filament 410 can be knotted 418 within large chamber 420. As long as the knotting 418 is larger than inner diameter 416, then insertion filament 410 cannot detach from coupler 402. A glue 422 can further be used to hold knotting 418 in place and/or the attach filament 400 to coupler 402.

Inner diameter 406 can be sized appropriate for a given filament outer diameter. For example, inner diameter 406 can be about 0.010 inches, about 0.012 inches, about 0.0150 inches, about 0.0155 inches, about 0.0145 inches, or about 0.0120 inches, about 0.0125 inches, about 0.05 inches, about 0.10 inches, or about 0.15 inches.

Inner diameter 416 can be sized appropriate for an insertion filament. For example, inner diameter 416 can be about 0.003, about 0.004 inches, about 0.005 inches or about 0.006 inches.

Coupler 402 can be formed of a plastic or other polymeric material such as, but not limited to rubber, synthetic rubber, silicone polymers, thermoplastics, thermosets, polyolefins, polyisobutylene, acrylic polymers, ethylene-co-vinylacetate, polybutylmethacrylate, vinyl halide polymers (for example, polyvinyl chloride), polyvinyl ethers (for example, polyvinyl methyl ether), polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides (for example, Nylon 66 and polycaprolactam), alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene (for example, Teflon) and combinations thereof. In one embodiment, a coupler is made of poly(ether-ether-ketone).

In some embodiments, a coupler can also be formed of metal such as, but not limited to aluminum, titanium, zinc, platinum, tantalum, copper, nickel, rhodium, gold, silver, palladium, chromium, iron, indium, ruthenium, osmium, tin, iridium, or combinations and alloys thereof. In some embodiments, a metal is not used if it interferes with imaging of the insertion procedure.

The glue 422 can be any glue that can hold knotting 418 in place and/or attach filament 400 without prematurely severing. The glue can include acrylates, cyanoacrylates, silicones, rubbers, polyurethanes, and combinations thereof. In one embodiment, the glue can be a UV curing glue. In another embodiment, the glue can be acrylate based.

In one embodiment, insertion filament can be fed through second end 412 of coupler 402 and tied into a knot. Then, a UV curable glue is applied over the knot and a filament is inserted until it touches the glue. A UV light can be applied to cure the glue over the knot and against the filament securing all together.

Subsequently, the coupler may be attached to a pusher, packaged, and sterilized. Upon receipt, the physician introduces the filament into a microcatheter or catheter and can then push it through the microcatheter or catheter to the embolization site. The filament can be advanced and withdrawn until the physician is satisfied with its position. Then the filament can then be detached from the pusher.

If a pushable device is desired, a dried hydrogel filament can be loaded into an introducer, packaged in a suitable pouch, and sterilized. Upon receipt, the physician transfers the filament from the introducer to a microcatheter or catheter using a guide wire, a fluid injection or a stylet. The dried hydrogel filament can then be pushed through the microcatheter or catheter and into the embolization site using a guide wire or a fluid injection.

A polymer or hydrogel filament, such as those described in the embodiments described above, may be difficult to track through a catheter since the entire filament is in contact with the inner diameter of the catheter, resulting in friction between the filament and the catheter. In some embodiments, the filament is a coil such as an embolic coil.

In some embodiments, an overcoil can be wound over or otherwise associated with at least a portion of an embolic coil or polymer filament thereby separating embolic coil contact points with the inside of the catheter and thus aid in trackability.

Figure 6:
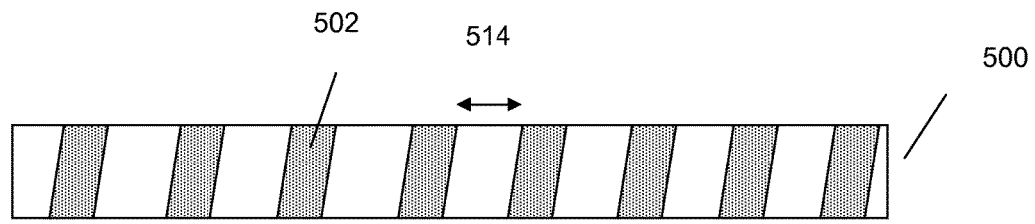
FIG. 6 illustrates an overcoil wound over a mandrel, said overcoil placed over an embolic coil.

In FIG. 6, an overcoil 502 is shown. Overcoil 502 may be wound over a mandrel 500 to create a coiled or helical shape. Overcoil 502 can then be thermally annealed to set the shape.

Once shaped to the desired dimensions, overcoil 502 can be slid over the full length of an implant and secured on both ends (i.e. via UV adhesive). Alternatively, overcoil 502 can be selectively placed over a portion of an implant.

Figure 7:
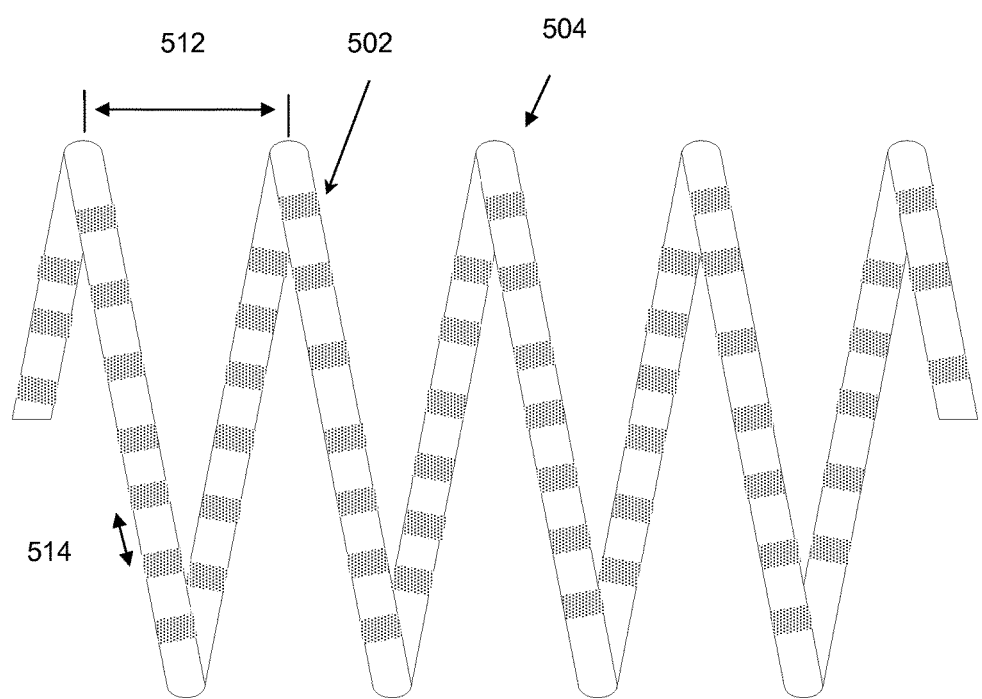
FIG. 7 illustrates an embolic coil with an overcoil placed over said embolic coil.

FIG. 7 illustrates overcoil 502 wound over embolic coil 504. Overcoil 502 may be used with polymer embolic coils, such as the ones described herein, as well as embolic coils comprising other materials (i.e. metallic). In one embodiment, an embolic coil may be metallic or include one or more metals.

Figure 8:
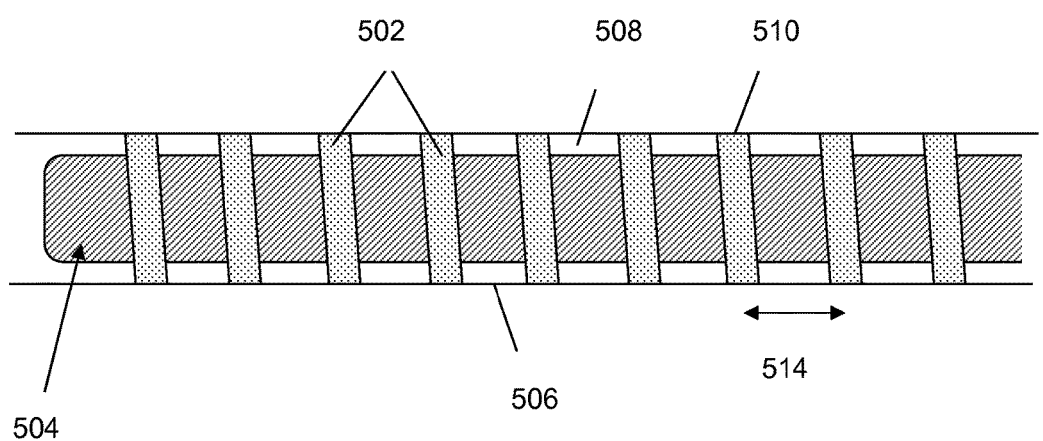
FIG. 8 illustrates an embolic coil with an overcoil in a catheter.

Overcoil 502, wound over embolic coil 504, can create contact area spacing 508 between embolic coil 504 and catheter inner wall 506, thus reducing overall friction and aiding in pushability. Contact area spacing 508 is shown in FIG. 8. Overcoil 502 sits over embolic coil 504, the overcoil distributes contact points 510 between embolic coil 504 and catheter inner wall 506.

Overcoil 502 can comprise a variety of materials. In one embodiment, overcoil 502 can include polymeric materials such as nylon, PEEK, PTFE, EPTFE, other polymers, or combinations thereof. In other embodiments, overcoil 502 can include metals or metallic materials such as stainless steel, nitinol, cobalt, chromium, or combinations thereof. In still other embodiments, overcoil 502 can include radiopaque materials such as tantalum, gold, platinum, barium, or combinations thereof. Overcoil can also include various combinations of polymeric materials, metals, and radiopaque materials.

In one example, the wound coil is placed over a polymeric embolic coil while said embolic coil is stretched or in tension. In another example the wound coil is placed over the polymeric embolic coil when the polymeric embolic coil is not in tension.

Though the overcoil can comprise a number of materials (including polymeric and/or metallic), as described above, a polymeric embolic coil would be particularly advantageous with a polymeric overcoil in order to maintain material consistency within the vasculature. However, as mentioned previously, various material combinations are possible with the overcoil and the embolic coil, and the overcoil is particularly useful in reducing the overall friction between the embolic coil and the inner surface of the catheter.

Though an overcoil is described, the overcoil may have a number of cross sectional shapes including circular, elliptical, rectangular, etc. The overcoil could also be a ribbon. The overcoil may be relatively closely wound or relatively loosely wound, depending on the material properties of the embolic coil as well as the frictional coefficient of the overcoil as well as that of the catheter. In one example, the overcoil is wound over a mandrel to create an overcoil has a pitch 514 of 0.05 to 0.09 inches, as shown in FIG. 6. The actual embolic coil the overcoil sits over may have a pitch 512 of 0 to 0.35 inches, as shown in FIG. 7. An embolic coil pitch close to zero would be substantially closed, meanings windings would sit directly adjacent to each other. For clarity, the pitch is defined as the length between successive windings. In FIG. 8, embolic coil 504 adopts an elongated shape when within the delivery catheter 506 and adopts a coiled configuration as shown in FIG. 7 once released from said catheter. The overcoil may be wound over a mandrel which approximates the diameter of the embolic coil in order to size the overcoil appropriately to the embolic coil. Thus the overcoil diameter mirrors the embolic coil diameter and can range anywhere from 0.002 inches to 0.1 inches, depending on the size of the embolic coil.

EXAMPLE 1

Preparation of Ethoxylated Trimethylolpropane Triacrylamide

First, 120 g of ethoxylated trimethylolpropane (TMP) 730 was dried by azeotropic distillation with 900 mL of toluene. Then, 82.4 mL of triethylamine was added with 46.8 mL of mesyl chloride and stirred for 12 hours. The solution was then filtered to remove any salt and the solvent evaporated. The resulting product was added to 600 mL of acetonitrile and 1500 mL of 25% ammonia hydroxide and stirred for 3 days. All but 200 mL of water was evaporated and the pH was adjusted to 13 with NaOH. The solution was extracted with dichloromethane, dried over magnesium sulfate, filtered and the solvent evaporated. The resulting ethoxylated trimethylolpropane amine was re-dissolved in 800 mL of dichloromethane and cooled in an ice bath. Then, 78 g of sodium carbonate was added along with 42 mL of acryloyl chloride and stirred for 18 hours. The solution was filtered to remove salt and the solvent evaporated. The resulting ethoxylated trimethylolpropane triacrylamide was then purified over a silica column.

EXAMPLE 2

Preparation of Hydrogel Filament—Fluoroscopy

To prepare a hydrogel filament visible under fluoroscopy, 10.8 g of ethoxylated trimethyloylpropane triacrylamide from Example 1, 0.75 g 2-hydroxyethyl methacrylate, 2.4 g N-tert-butylacrylamide, 0.21 g methylenebisacrylamide and 0.14 g 2,2'-azobisisobutyronitrile were dissolved in 7.5 g of isopropyl alcohol. The solution was filtered through a 0.2 micron filter. To 18.2 g of the solution, 21.3 g of barium sulfate was added. The solution was sparged with argon for 10 min before injection into oval HYTREL® tubing wrapped around a mandrel. The tubes were heat sealed at both ends and placed in a 100° C. water bath for 1 hour, then overnight in an 80° C. oven to polymerize the solution.

The resulting hydrogel was removed by dissolving the tubing in a solution of 20% phenol in chloroform. After the tubing was removed, the phenol solution was exchanged with chloroform and washed for 1 hr. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

EXAMPLE 3

Preparation of Hydrogel Filament Device

The hydrogel filament of Example 2 can be attached to a V-TRAK® (MicroVention Terumo, Inc., Tustin, Calif.). To attach the hydrogel to a V-TRAK® pusher, a section of 0.0022 inch polyolefin thread was threaded through a coupler. The coupler consisted of a PEEK cylinder hollowed out on one end to accept the hydrogel filament and a through hole. The polyolefin thread was tied into a knot such that it could not be pulled back through. The hydrogel was glued into the coupler on top of the knot using adhesive. The other end of the polyolefin thread was threaded into a V-TRAK® pusher and tied.

EXAMPLE 4

In Vivo Evaluation of Hydrogel Filament Device

Twelve surgically created rabbit bifurcation aneurysms were embolized with radiopaque polymer filaments. The aneurysm width, length, and neck ranged from 1.7 to 11.8 mm. Under fluoroscopic guidance, a microcatheter (Headway®, MicroVention Terumo, Inc., Tustin, Calif.) was placed inside the aneurysm sac. Several radiopaque hydrogel filaments were deployed inside the aneurysm sac. Six of the aneurysms were embolized as completely as possible while the remaining 6 were incompletely embolized to ensure blood filling in the neck. At four and 13 weeks post-embolization, stable occlusion of all 12 aneurysms was demonstrated by angiography. The aneurysms were harvested and histologically processed. The aneurysm sacs were filled with the radiopaque hydrogel filaments and mixtures of fibrovascular tissue and unorganized thrombus. The necks were almost completely to completely traversed with an endothelialized neointima. Inflammation was minimal to mild. These results illustrated that the radiopaque hydrogel filaments can be deployed into experimental aneurysms and elicit a foreign body response consistent with other embolic devices.

CT Evaluation of Hydrogel Filament Device

Twelve surgically created rabbit bifurcation aneurysms embolized with radiopaque polymer filaments underwent CT angiography follow up at 4 and 13 weeks post-embolization. CTA was performed using a 10-multisectional helical CT machine (Brilliance 10: Philips Healthcare). Contrast was administered through a cannula in the ear vein. When imaged, the beam-hardening artifacts of the hydrogel filaments were greatly reduced compared to previously imaged platinum coils. The embolus, individual coils, and neck remnants were visible with CTA. CTA imaging can be suitable for determining if re-treatment is necessary for aneurysms embolized with radiopaque hydrogel filaments.

MR Evaluation of Hydrogel Filament Device

Twelve surgically created rabbit bifurcation aneurysms embolized with radiopaque polymer filaments underwent MR angiography follow up at 4 and 13 weeks post-embolization. The aneurysms were imaged with a 3T scanner (Magnetom Trio; Siemens) using a 3D time-of-flight sequence. Only the neck remnants were visible with MRA, similar to platinum coils. MRA imaging can be suitable for determining if re-treatment is necessary for aneurysms embolized with radiopaque hydrogel filaments.

EXAMPLE 5

In Vitro Evaluation of the Bending Resistance of the Hydrogel Filament

The bending resistance of the hydrogel filaments of the formulation in Example 2 was measured. The hydrogels were prepared in tubing of various diameters. Measurements were obtained using a Gurley 4171 ET tubular sample stiffness tester with a 5 g counterweight attached to its measuring vane. The sample length was one inch. The bending resistance was measured in the dry state as well as after 30 seconds of hydration with 0.9% saline. The average of three to five replicates each are summarized in the following table.

| Sample | Measured Resistance (mg) Dry | Measured Resistance (mg) Hydrated for 30 seconds |
|---|---|---|
| 0.0055" | 0.49 ± 0.27 | 0.28 ± 0.12 |
| 0.010" | 1.11 ± 0.23 | 0.28 ± 0.07 |
| 0.017" | 6.67 ± 0.60 | 4.73 ± 0.88 |
| 0.018" | 9.04 ± 0.16 | 7.78 ± 0.23 |
| 0.020" | 10.56 ± 0.79 | 8.62 ± 0.72 |
| 0.025" | 19.07 ± 0.98 | 17.38 ± 1.17 |
| 0.030" | 36.39 ± 1.53 | 29.40 ± 1.90 |
| 0.035" | 63.68 ± 1.46 | 59.10 ± 4.74 |
| 0.040" | 128.21 ± 0.79 | 121.58 ± 1.31 |
| 0.080" | 1,021.20 ± 69.62 | 860.25 ± 54.76 |

The results illustrate the range of bending resistances achievable.

EXAMPLE 6

In Vitro Evaluation of the Ultimate Tensile Strength of the Hydrogel Filament

The ultimate tensile strength of hydrogel filaments prepared in tubings of various diameters of the formulation in Example 2 were obtained using an Instron 5543. The ultimate tensile strength was measured in the dry state as well as after one hour of hydration with 0.9% saline (full hydration). The average of three to five replicates each are summarized in the following table.

| Sample | Tensile Strength (lbf) Dry | Tensile Strength (lbf) Hydrated |
|---|---|---|
| 0.0055" | 0.033 ± 0.002 | 0.009 ± 0.002 |
| 0.010" | 0.072 ± 0.010 | 0.039 ± 0.006 |
| 0.017" | 0.247 ± 0.024 | 0.138 ± 0.014 |
| 0.018" | 0.298 ± 0.006 | 0.132 ± 0.021 |
| 0.020" | 0.268 ± 0.030 | 0.134 ± 0.037 |
| 0.025" | 0.443 ± 0.060 | 0.225 ± 0.016 |
| 0.030" | 0.577 ± 0.055 | 0.271 ± 0.057 |
| 0.035" | 0.415 ± 0.101 | 0.300 ± 0.097 |
| 0.040" | 1.250 ± 0.136 | 0.513 ± 0.093 |
| 0.080" | 2.572 ± 0.576 | 1.055 ± 0.200 |

The results illustrate the range of ultimate tensile strengths achievable.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An implantable coil comprising:
   a shapeable polymeric filament formed from a combination of precursors comprising a trimethylolpropane ethoxylate triacrylamide macromer; t-butyl acrylamide monomer and a hydroxyethyl methacrylate monomer; and a crosslinker; and comprising at least one visualization agent; and
   an overcoil wrapped multiple times around at least a portion of the shapeable polymeric filament, the overcoil configured to create contact area spacing between the filament and a delivery catheter.

2. The implantable coil according to claim 1, having reduced beam hardening artifacts when imaged using computed tomography.

3. The implantable coil according to claim 1, wherein the at least one visualization agent is selected from metallic powders, gadolinium, superparamagnetic iron oxide particles, barium sulfate or a combination thereof.

4. The implantable coil according to claim 1, wherein the polymeric filament has a diameter of less than about 0.03 inches.

5. The implantable coil according to claim 1, wherein the polymeric filament is non-resorbable by body tissues.

6. The implantable coil according to claim 1, wherein the polymeric filament is biodegradable.

7. The implantable coil according to claim 1, wherein the trimethylolpropane ethoxylate triacrylamide macromer is trimethylolpropane ethoxylate triacrylamide having a molecular weight of 900 g/mol.

8. The implantable coil according to claim 1, wherein the cross-linker is N,N'-methylenebisacrylamide.

9. An implantable coil including:
   a hydrogel filament consisting essentially of about 27% w/w trimethylolpropane ethoxylate triacrylamide 900, about 6% w/w t-butyl acrylamide, about 2% hydroxyethyl methacrylate, about 0.5% w/w N,N-methylenebisacrylamide, about 64% barium sulfate, and about 0.5% 2,2'-azobisisobutyronitrile, and
   an overcoil wrapped multiple times around at least a portion of the filament, the overcoil configured to create contact area spacing between the filament and a delivery catheter.

10. An implantable coil including:
a hydrogel filament consisting essentially of about 30% w/w trimethylolpropane ethoxylate triacrylamide 900, about 6% w/w t-butyl acrylamide, about 2% hydroxyethyl methacrylate, about 0.75% w/w N,N-methylenebisacrylamide, about 48% barium sulfate, and about 0.5% 2,2'-azobisisobutyronitrile, and
an overcoil wrapped multiple times around at least a portion of the filament, the overcoil configured to create contact area spacing between the filament and a delivery catheter.

11. The implantable coil according to claim 1, wherein the overcoil is formed of a polymeric material or a metallic material.

12. The implantable coil according to claim 11, wherein the polymeric material includes nylon, PEEK, PTFE, EPTFE, or a combination thereof, or wherein the metallic material includes stainless steel, nitinol, cobalt, chromium, tantalum, gold, platinum, barium, or a combination thereof.

* * * * *